United States Patent
Owen et al.

(10) Patent No.: US 11,996,176 B2
(45) Date of Patent: *May 28, 2024

(54) AMBIENT CLINICAL INTELLIGENCE SYSTEM AND METHOD

(71) Applicant: Microsoft Technology Licensing, LLC, Redmond, WA (US)

(72) Inventors: Donald E. Owen, Orlando, FL (US); Guido Remi Marcel Gallopyn, Newburyport, MA (US); Paul Joseph Vozila, Arlington, MA (US); Mehmet Mert Öz, Baden (AT); Matthieu Hebert, Beauharnois (CA)

(73) Assignee: Microsoft Technology Licensing, LLC, Redmond, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/577,419

(22) Filed: Jan. 18, 2022

(65) Prior Publication Data

US 2022/0139516 A1    May 5, 2022

Related U.S. Application Data

(63) Continuation of application No. 16/442,247, filed on Jun. 14, 2019, now Pat. No. 11,227,679.

(51) Int. Cl.
| | | |
|---|---|---|
| G06F 16/45 | (2019.01) | |
| G06V 20/40 | (2022.01) | |
| G10L 15/26 | (2006.01) | |
| G16H 10/60 | (2018.01) | |
| G16H 15/00 | (2018.01) | |
| G16H 20/40 | (2018.01) | |
| G16H 40/20 | (2018.01) | |

(52) U.S. Cl.
CPC .............. *G16H 15/00* (2018.01); *G06V 20/41* (2022.01); *G10L 15/26* (2013.01); *G16H 10/60* (2018.01); *G16H 40/20* (2018.01)

(58) Field of Classification Search
CPC ........ G16H 15/00; G16H 10/60; G16H 40/20; G06V 20/41; G06V 20/52; G06V 40/23; G10L 15/26; G10L 2021/02166
See application file for complete search history.

(56) References Cited

U.S. PATENT DOCUMENTS

| | | |
|---|---|---|
| 2014/0330586 A1 | 11/2014 | Riskin et al. |
| 2017/0061081 A1 | 3/2017 | Jagannathan et al. |
| 2017/0289503 A1 | 10/2017 | Kusens |
| 2018/0287976 A1* | 10/2018 | Hochstein ............... H04W 4/18 |
| 2019/0253668 A1* | 8/2019 | Kusens ................. G06V 20/52 |
| 2020/0372998 A1* | 11/2020 | Venkataraman ....... G16H 20/40 |

OTHER PUBLICATIONS

"Extended Search Report Issued in European Patent Application No. 20822473.3", dated May 16, 2023, 9 Pages.

* cited by examiner

*Primary Examiner* — Maroun P Kanaan
(74) *Attorney, Agent, or Firm* — Brian J. Colandreo; Heath M. Sargeant; Holland & Knight LLP

(57) ABSTRACT

A method, computer program product, and computing system for obtaining encounter information during a patient encounter; processing the encounter information to detect the execution of a physical event during the patient encounter, thus defining a detected physical event; and deriving information for the detected physical event.

15 Claims, 8 Drawing Sheets

AMBIENT CLINICAL INTELLIGENCE SYSTEM AND METHOD

RELATED APPLICATION

This application is a continuation of U.S. patent application Ser. No. 16/442,247 filed Jun. 14, 2019, the contents of which is incorporated herein by reference.

TECHNICAL FIELD

This disclosure relates to intelligence systems and methods and, more particularly, to ambient clinical intelligence systems and methods.

BACKGROUND

As is known in the art, clinical intelligence is the creation of medical reports and documentation that details the medical history of medical patients. As would be expected, traditional clinical documentation includes various types of data, examples of which may include but are not limited to paper-based documents and transcripts, as well as various images and diagrams.

As the world moved from paper-based content to digital content, clinical documentation also moved in that direction, where medical reports and documentation were gradually transitioned from stacks of paper geographically-dispersed across multiple locations/institutions to consolidated and readily accessible digital content.

SUMMARY OF DISCLOSURE

In one implementation, a computer-implemented method is executed on a computing device and includes: obtaining encounter information during a patient encounter; processing the encounter information to detect the execution of a physical event during the patient encounter, thus defining a detected physical event; and deriving information for the detected physical event.

One or more of the following features may be included. Obtaining encounter information during a patient encounter may include: utilizing a machine vision system to obtain machine vision encounter information during the patient encounter. Deriving information for the detected physical event may include: generating a text-based description of the detected physical event; and annotating a medical record to include the text-based description of the detected physical event. Deriving information for the detected physical event may include: associating the detected physical event with a defined procedure; and memorializing the execution of the defined procedure. Deriving information for the detected physical event may include: determining the appropriateness of the detected physical event. Determining the appropriateness of the detected physical event may include one or more of: determining whether the detected physical event violates any professional rules; determining whether the detected physical event violates any civil rules; and determining whether the detected physical event violates any criminal laws. The detected physical event may be associable with a verbal component. The detected physical event may include the use of a physical device. The information derived for the detected physical event may include: machine vision encounter information; and audio encounter information. The encounter information may include one or more of: machine vision encounter information; and audio encounter information.

In another implementation, a computer program product resides on a computer readable medium and has a plurality of instructions stored on it. When executed by a processor, the instructions cause the processor to perform operations including obtaining encounter information during a patient encounter; processing the encounter information to detect the execution of a physical event during the patient encounter, thus defining a detected physical event; and deriving information for the detected physical event.

One or more of the following features may be included. Obtaining encounter information during a patient encounter may include: utilizing a machine vision system to obtain machine vision encounter information during the patient encounter. Deriving information for the detected physical event may include: generating a text-based description of the detected physical event; and annotating a medical record to include the text-based description of the detected physical event. Deriving information for the detected physical event may include: associating the detected physical event with a defined procedure; and memorializing the execution of the defined procedure. Deriving information for the detected physical event may include: determining the appropriateness of the detected physical event. Determining the appropriateness of the detected physical event may include one or more of: determining whether the detected physical event violates any professional rules; determining whether the detected physical event violates any civil rules; and determining whether the detected physical event violates any criminal laws. The detected physical event may be associable with a verbal component. The detected physical event may include the use of a physical device. The information derived for the detected physical event may include: machine vision encounter information; and audio encounter information. The encounter information may include one or more of: machine vision encounter information; and audio encounter information.

In another implementation, a computing system includes a processor and memory is configured to perform operations including obtaining encounter information during a patient encounter; processing the encounter information to detect the execution of a physical event during the patient encounter, thus defining a detected physical event; and deriving information for the detected physical event.

One or more of the following features may be included. Obtaining encounter information during a patient encounter may include: utilizing a machine vision system to obtain machine vision encounter information during the patient encounter. Deriving information for the detected physical event may include: generating a text-based description of the detected physical event; and annotating a medical record to include the text-based description of the detected physical event. Deriving information for the detected physical event may include: associating the detected physical event with a defined procedure; and memorializing the execution of the defined procedure. Deriving information for the detected physical event may include: determining the appropriateness of the detected physical event. Determining the appropriateness of the detected physical event may include one or more of: determining whether the detected physical event violates any professional rules; determining whether the detected physical event violates any civil rules; and determining whether the detected physical event violates any criminal laws. The detected physical event may be associable with a verbal component. The detected physical event may include the use of a physical device. The information derived for the detected physical event may include: machine vision encounter information; and audio encounter information. The encounter information may include one or more of: machine vision encounter information; and audio encounter information.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

System Overview

Figure 1:
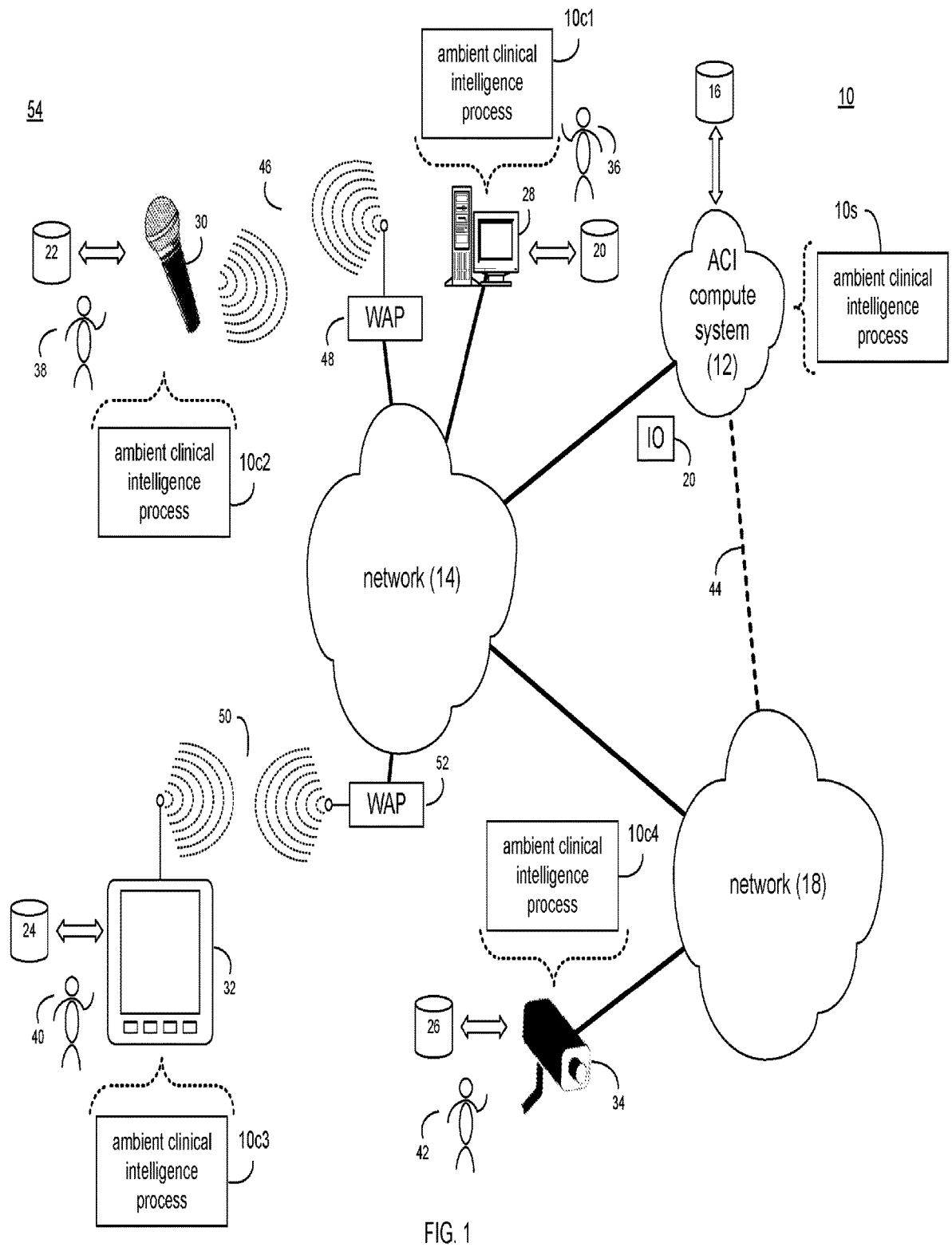
FIG. 1 is a diagrammatic view of an ambient clinical intelligence compute system and an ambient clinical intelligence process coupled to a distributed computing network.

Referring to FIG. 1, there is shown ambient clinical intelligence process 10. As will be discussed below in greater detail, ambient clinical intelligence process 10 may be configured to automate the collection and processing of clinical encounter information to generate/store/distribute medical reports.

Ambient clinical intelligence process 10 may be implemented as a server-side process, a client-side process, or a hybrid server-side/client-side process. For example, ambient clinical intelligence process 10 may be implemented as a purely server-side process via ambient clinical intelligence process 10s. Alternatively, ambient clinical intelligence process 10 may be implemented as a purely client-side process via one or more of ambient clinical intelligence process 10c1, ambient clinical intelligence process 10c2, ambient clinical intelligence process 10c3, and ambient clinical intelligence process 10c4. Alternatively still, ambient clinical intelligence process 10 may be implemented as a hybrid server-side/client-side process via ambient clinical intelligence process 10s in combination with one or more of ambient clinical intelligence process 10c1, ambient clinical intelligence process 10c2, ambient clinical intelligence process 10c3, and ambient clinical intelligence process 10c4.

Accordingly, ambient clinical intelligence process 10 as used in this disclosure may include any combination of ambient clinical intelligence process 10s, ambient clinical intelligence process 10c1, ambient clinical intelligence process 10c2, ambient clinical intelligence process 10c3, and ambient clinical intelligence process 10c4.

Ambient clinical intelligence process 10s may be a server application and may reside on and may be executed by ambient clinical intelligence (ACI) compute system 12, which may be connected to network 14 (e.g., the Internet or a local area network). ACI compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACI compute system 12 may execute one or more operating systems, examples of which may include but are not limited to: Microsoft Windows Server™; Redhat Linux™, Unix, or a custom operating system, for example.

The instruction sets and subroutines of ambient clinical intelligence process 10s, which may be stored on storage device 16 coupled to ACI compute system 12, may be executed by one or more processors (not shown) and one or more memory architectures (not shown) included within ACI compute system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from ambient clinical intelligence process 10s, ambient clinical intelligence process 10c1, ambient clinical intelligence process 10c2, ambient clinical intelligence process 10c3 and/or ambient clinical intelligence process 10c4 to ACI compute system 12. Examples of IO request 20 may include but are not limited to data write requests (i.e. a request that content be written to ACI compute system 12) and data read requests (i.e. a request that content be read from ACI compute system 12).

The instruction sets and subroutines of ambient clinical intelligence process 10c1, ambient clinical intelligence process 10c2, ambient clinical intelligence process 10c3 and/or ambient clinical intelligence process 10c4, which may be stored on storage devices 20, 22, 24, 26 (respectively) coupled to ACI client electronic devices 28, 30, 32, 34 (respectively), may be executed by one or more processors (not shown) and one or more memory architectures (not shown) incorporated into ACI client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACI client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACI compute system 12 directly through network 14 or through secondary network 18. Further, ACI compute system 12 may be connected to network 14 through secondary network 18, as illustrated with link line 44.

The various ACI client electronic devices (e.g., ACI client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACI client electronic devices (e.g., ACI client electronic devices 28, 30, 32, 34) may each execute an operating system, examples of which may include but are not limited to Microsoft Windows™, Apple Macintosh™, Redhat Linux™, or a custom operating system, wherein the combination of the various ACI client electronic devices (e.g., ACI client electronic devices 28, 30, 32, 34) and ACI compute system 12 may form modular ACI system 54.

The Ambient Clinical Intelligence System

Figure 2:
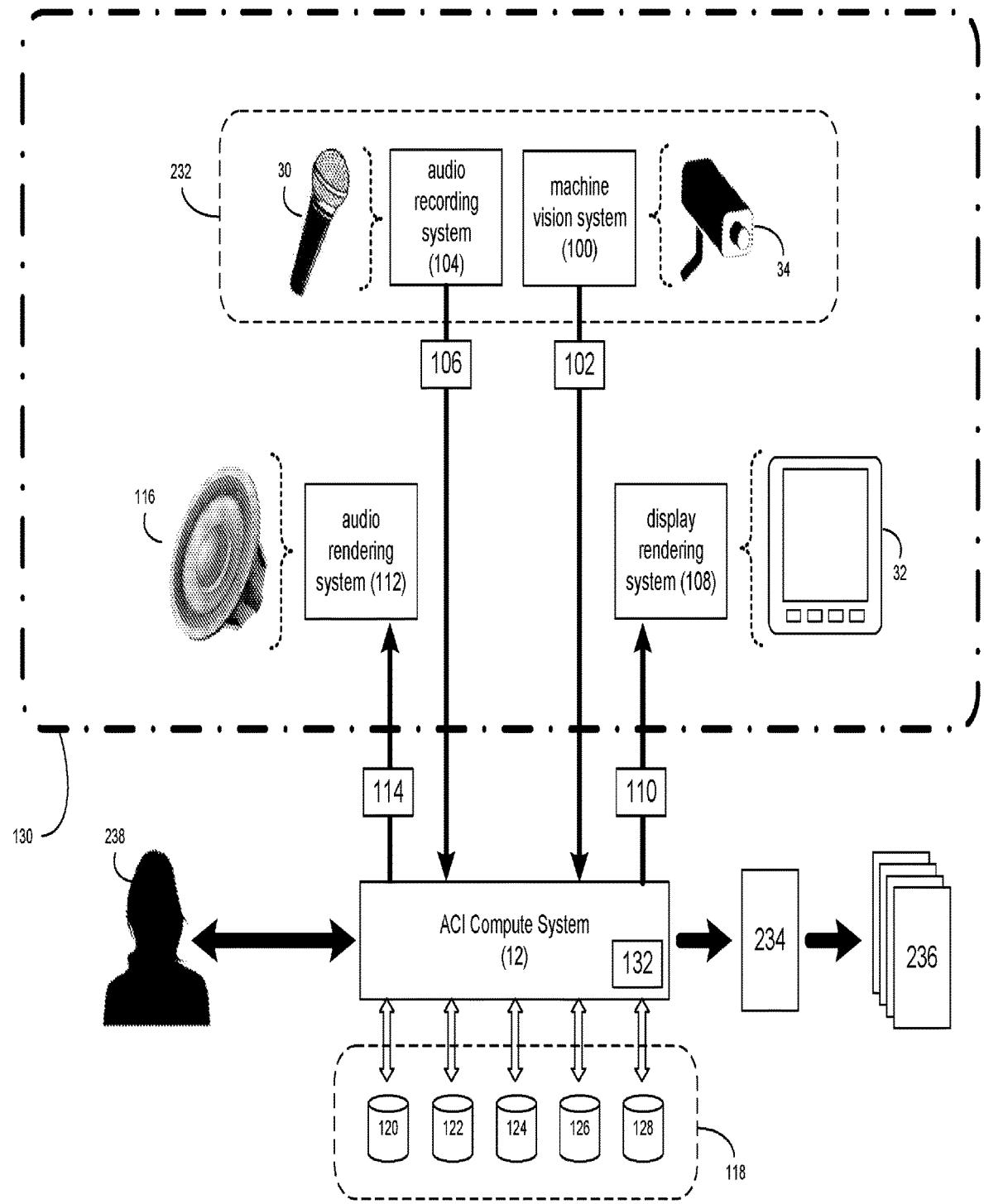
FIG. 2 is a diagrammatic view of a modular ACI system incorporating the ambient clinical intelligence compute system of FIG. 1.

Referring also to FIG. 2, there is shown a simplified exemplary embodiment of modular ACI system 54 that is configured to automate clinical documentation. Modular ACI system 54 may include: machine vision system 100 configured to obtain machine vision encounter information 102 concerning a patient encounter; audio recording system 104 configured to obtain audio encounter information 106 concerning the patient encounter; and a compute system (e.g., ACI compute system 12) configured to receive machine vision encounter information 102 and audio encounter information 106 from machine vision system 100 and audio recording system 104 (respectively). Modular ACI system 54 may also include: display rendering system 108 configured to render visual information 110; and audio rendering system 112 configured to render audio information 114, wherein ACI compute system 12 may be configured to provide visual information 110 and audio information 114 to display rendering system 108 and audio rendering system 112 (respectively).

Example of machine vision system 100 may include but are not limited to: one or more ACI client electronic devices (e.g., ACI client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACI client electronic devices (e.g., ACI client electronic device 30, examples of which may include but are not limited to a handheld microphone (e.g., one example of a body worn microphone), a lapel microphone (e.g., another example of a body worn microphone), an embedded microphone, such as those embedded within eyeglasses, smart phones, tablet computers and/or watches (e.g., another example of a body worn microphone), and an audio recording device). Examples of display rendering system 108 may include but are not limited to: one or more ACI client electronic devices (e.g., ACI client electronic device 32, examples of which may include but are not limited to a tablet computer, a computer monitor, and a smart television). Examples of audio rendering system 112 may include but are not limited to: one or more ACI client electronic devices (e.g., audio rendering device 116, examples of which may include but are not limited to a speaker system, a headphone system, and an earbud system).

ACI compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the ambient speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource. While in this particular example, five different examples of datasources 118 are shown, this is for illustrative purposes only and is not intended to be a limitation of this disclosure, as other configurations are possible and are considered to be within the scope of this disclosure.

As will be discussed below in greater detail, modular ACI system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACI client electronic devices (e.g., ACI client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACI client electronic devices (e.g., ACI client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACI client electronic devices (e.g., ACI client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACI client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACI compute system 12 may include a plurality of discrete compute systems. As discussed above, ACI compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACI compute system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Microphone Array

Figure 3:
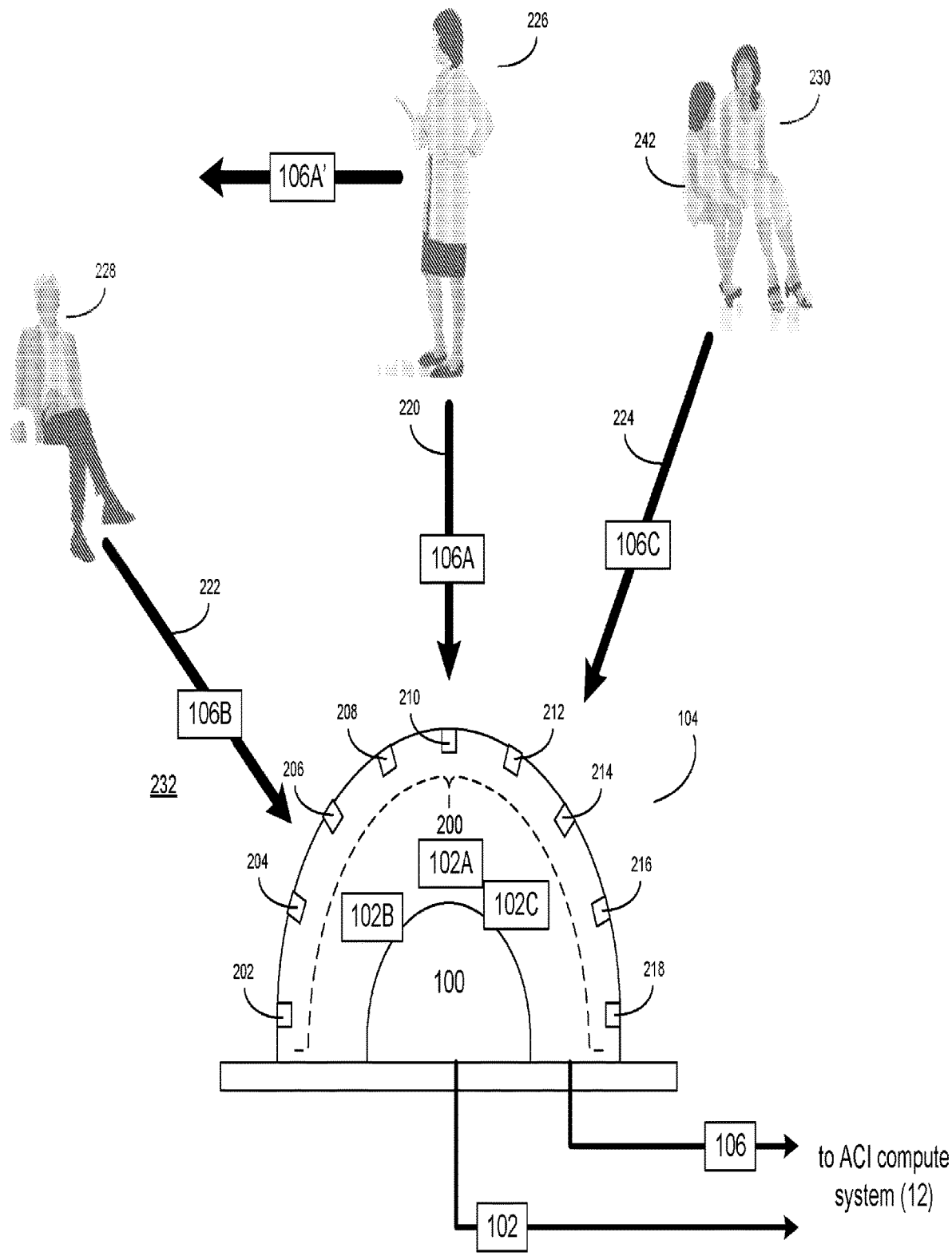
FIG. 3 is a diagrammatic view of a mixed-media ACI device included within the modular ACI system of FIG. 2.

Referring also to FIG. 3, audio recording system 104 may include microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACI system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACI system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACI system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACI system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACI system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230). Further, modular ACI system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference. In particular, null-steering precoding may be a method of beamforming for narrowband signals that may compensate for delays of receiving signals from a specific source at different elements of an antenna array. In general and to improve performance of the antenna array, incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACI device 232. For example, mixed-media ACI device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACI system 54 may be configured to include a plurality of mixed-media ACI devices (e.g., mixed-media ACI device 232) when the above-described clinical environment is larger or a higher level of resolution is desired.

Modular ACI system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACI device 232 (and machine vision system 100/audio recording system 104 included therein) may be configured to monitor one or more encounter participants (e.g., encounter participants 226, 228, 230) of a patient encounter.

Specifically and as will be discussed below in greater detail, machine vision system 100 (either as a stand-alone system or as a component of mixed-media ACI device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACI compute system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACI system 54 (and/or mixed-media ACI device 232) is configured, ACI compute system 12 may be included within mixed-media ACI device 232 or external to mixed-media ACI device 232.

The Ambient Clinical Intelligence Process

As discussed above, ACI compute system 12 may execute all or a portion of ambient clinical intelligence process 10, wherein the instruction sets and subroutines of ambient clinical intelligence process 10 (which may be stored on one or more of e.g., storage devices 16, 20, 22, 24, 26) may be executed by ACI compute system 12 and/or one or more of ACI client electronic devices 28, 30, 32, 34.

Figure 4:
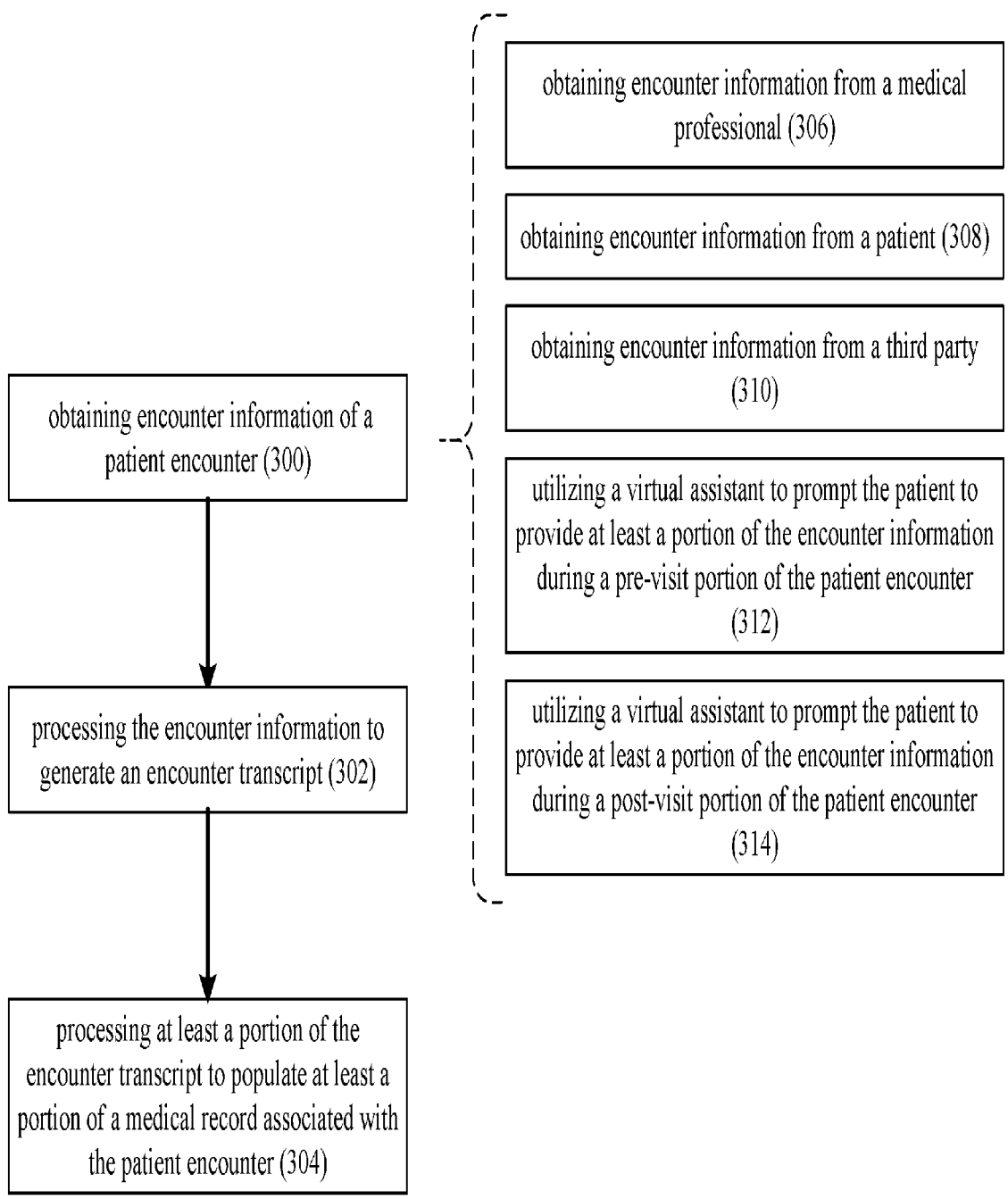
FIG. 4 is a flow chart of one implementation of the ambient clinical intelligence process of FIG. 1.

As discussed above, ambient clinical intelligence process 10 may be configured to automate the collection and processing of clinical encounter information to generate/store/distribute medical records. Accordingly and referring also to FIG. 4, ambient clinical intelligence process 10 may be configured to obtain 300 encounter information (e.g., machine vision encounter information 102 and/or audio encounter information 106) of a patient encounter (e.g., a visit to a doctor's office). Ambient clinical intelligence process 10 may further be configured to process 302 the encounter information (e.g., machine vision encounter information 102 and/or audio encounter information 106) to generate an encounter transcript (e.g., encounter transcript 234), wherein ambient clinical intelligence process 10 may then process 304 at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, ambient clinical intelligence process 10 may utilize these corrections for training/tuning purposes (e.g., to adjust the various profiles associated the participants of the patient encounter) to enhance the future accuracy/efficiency/performance of ambient clinical intelligence process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, ambient clinical intelligence process 10 may utilize these corrections for training/tuning purposes (e.g., to adjust the various profiles associated the participants of the patient encounter) to enhance the future accuracy/efficiency/performance of ambient clinical intelligence process 10.

For example, assume that a patient (e.g., encounter participant 228) visits a clinical environment (e.g., a doctor's office) because they do not feel well. They have a headache, fever, chills, a cough, and some difficulty breathing. In this particular example, a monitored space (e.g., monitored space 130) within the clinical environment (e.g., the doctor's office) may be outfitted with machine vision system 100 configured to obtain machine vision encounter information 102 concerning the patient encounter (e.g., encounter participant 228 visiting the doctor's office) and audio recording system 104 configured to obtain audio encounter information 106 concerning the patient encounter (e.g., encounter participant 228 visiting the doctor's office) via one or more audio sensors (e.g., audio acquisition devices 202, 204, 206, 208, 210, 212, 214, 216, 218).

As discussed above, machine vision system 100 may include a plurality of discrete machine vision systems if the monitored space (e.g., monitored space 130) within the clinical environment (e.g., the doctor's office) is larger or a higher level of resolution is desired, wherein examples of machine vision system 100 may include but are not limited to: an RGB imaging system, an infrared imaging system, an ultraviolet imaging system, a laser imaging system, a SONAR imaging system, a RADAR imaging system, and a thermal imaging system. Accordingly and in certain instances/embodiments, machine vision system 100 may include one or more of each of an RGB imaging system, an infrared imaging system, an ultraviolet imaging system, a laser imaging system, a SONAR imaging system, a RADAR imaging system, and a thermal imaging system positioned throughout monitored space 130, wherein each of these systems may be configured to provide data (e.g., machine vision encounter information 102) to ACI compute system 12 and/or modular ACI system 54.

As also discussed above, audio recording system 104 may include a plurality of discrete audio recording systems if the monitored space (e.g., monitored space 130) within the clinical environment (e.g., the doctor's office) is larger or a higher level of resolution is desired, wherein examples of audio recording system 104 may include but are not limited to: a handheld microphone, a lapel microphone, an embedded microphone (such as those embedded within eyeglasses, smart phones, tablet computers and/or watches) and an audio recording device. Accordingly and in certain instances/embodiments, audio recording system 104 may include one or more of each of a handheld microphone, a lapel microphone, an embedded microphone (such as those embedded within eyeglasses, smart phones, tablet computers and/or watches) and an audio recording device positioned throughout monitored space 130, wherein each of these microphones/devices may be configured to provide data (e.g., audio encounter information 106) to ACI compute system 12 and/or modular ACI system 54.

Since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and via machine vision encounter information 102, visual speech recognition (via visual lip reading functionality) may be utilized by ambient clinical intelligence process 10 to further effectuate the gathering of audio encounter information 106.

Accordingly and when obtaining 300 encounter information (e.g., machine vision encounter information 102 and/or audio encounter information 106), ambient clinical intelligence process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), ambient clinical intelligence process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by ambient clinical intelligence process 10.

When ambient clinical intelligence process 10 obtains 300 the encounter information, ambient clinical intelligence process 10 may utilize 312 a virtual assistant (e.g., virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office).

Further and when ambient clinical intelligence process 10 obtains 300 encounter information, ambient clinical intelligence process 10 may utilize 314 a virtual assistant (e.g., virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office).

Automated Transcript Generation

Ambient clinical intelligence process 10 may be configured to process the encounter information (e.g., machine vision encounter information 102 and/or audio encounter information 106) to generate encounter transcript 234 that may be automatically formatted and punctuated.

Figure 5:
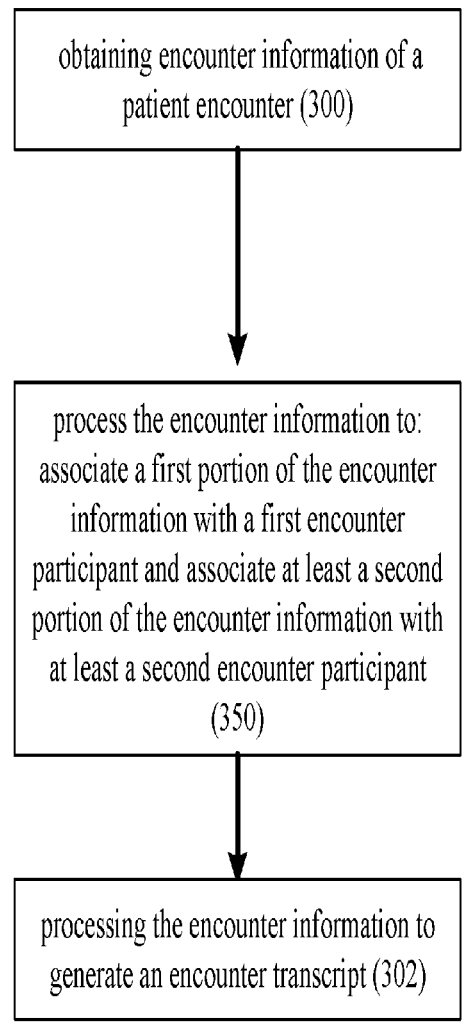
FIG. 5 is a flow chart of another implementation of the ambient clinical intelligence process of FIG. 1.

Accordingly and referring also to FIG. 5, ambient clinical intelligence process 10 may be configured to obtain 300 encounter information (e.g., machine vision encounter information 102 and/or audio encounter information 106) of a patient encounter (e.g., a visit to a doctor's office).

Ambient clinical intelligence process 10 may process 350 the encounter information (e.g., machine vision encounter information 102 and/or audio encounter information 106) to: associate a first portion of the encounter information (e.g., machine vision encounter information 102 and/or audio encounter information 106) with a first encounter participant, and associate at least a second portion of the encounter information (e.g., machine vision encounter information 102 and/or audio encounter information 106) with at least a second encounter participant.

As discussed above, modular ACI system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein modular ACI system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, modular ACI system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACI compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource.

Accordingly, ambient clinical intelligence process 10 may process 350 the encounter information (e.g., machine vision encounter information 102 and/or audio encounter information 106) to: associate a first portion (e.g., encounter information 106A) of the encounter information (e.g., audio encounter information 106) with a first encounter participant (e.g., encounter participant 226), and associate at least a second portion (e.g., encounter information 106B, 106C) of the encounter information (e.g., audio encounter information 106) with at least a second encounter participant (e.g., encounter participants 228, 230; respectively).

Further and when processing 350 the encounter information (e.g., audio encounter information 106A, 106B, 106C), ambient clinical intelligence process 10 may compare each of audio encounter information 106A, 106B, 106C to the voice prints defined within the above-referenced voice print datasource so that the identity of encounter participants 226, 228, 230 (respectively) may be determined. Accordingly, if the voice print datasource includes a voice print that corresponds to one or more of the voice of encounter participant 226 (as heard within audio encounter information 106A), the voice of encounter participant 228 (as heard within audio encounter information 106B) or the voice of encounter participant 230 (as heard within audio encounter information 106C), the identity of one or more of encounter participants 226, 228, 230 may be defined. And in the event that a voice heard within one or more of audio encounter information 106A, audio encounter information 106B or audio encounter information 106C is unidentifiable, that one or more particular encounter participant may be defined as "Unknown Participant".

Once the voices of encounter participants 226, 228, 230 are processed 350, ambient clinical intelligence process 10 may generate 302 an encounter transcript (e.g., encounter transcript 234) based, at least in part, upon the first portion of the encounter information (e.g., audio encounter information 106A) and the at least a second portion of the encounter information (e.g., audio encounter information 106B. 106C).

Automated Role Assignment

Ambient clinical intelligence process 10 may be configured to automatically define roles for the encounter participants (e.g., encounter participants 226, 228, 230) in the patient encounter (e.g., a visit to a doctor's office).

Figure 6:
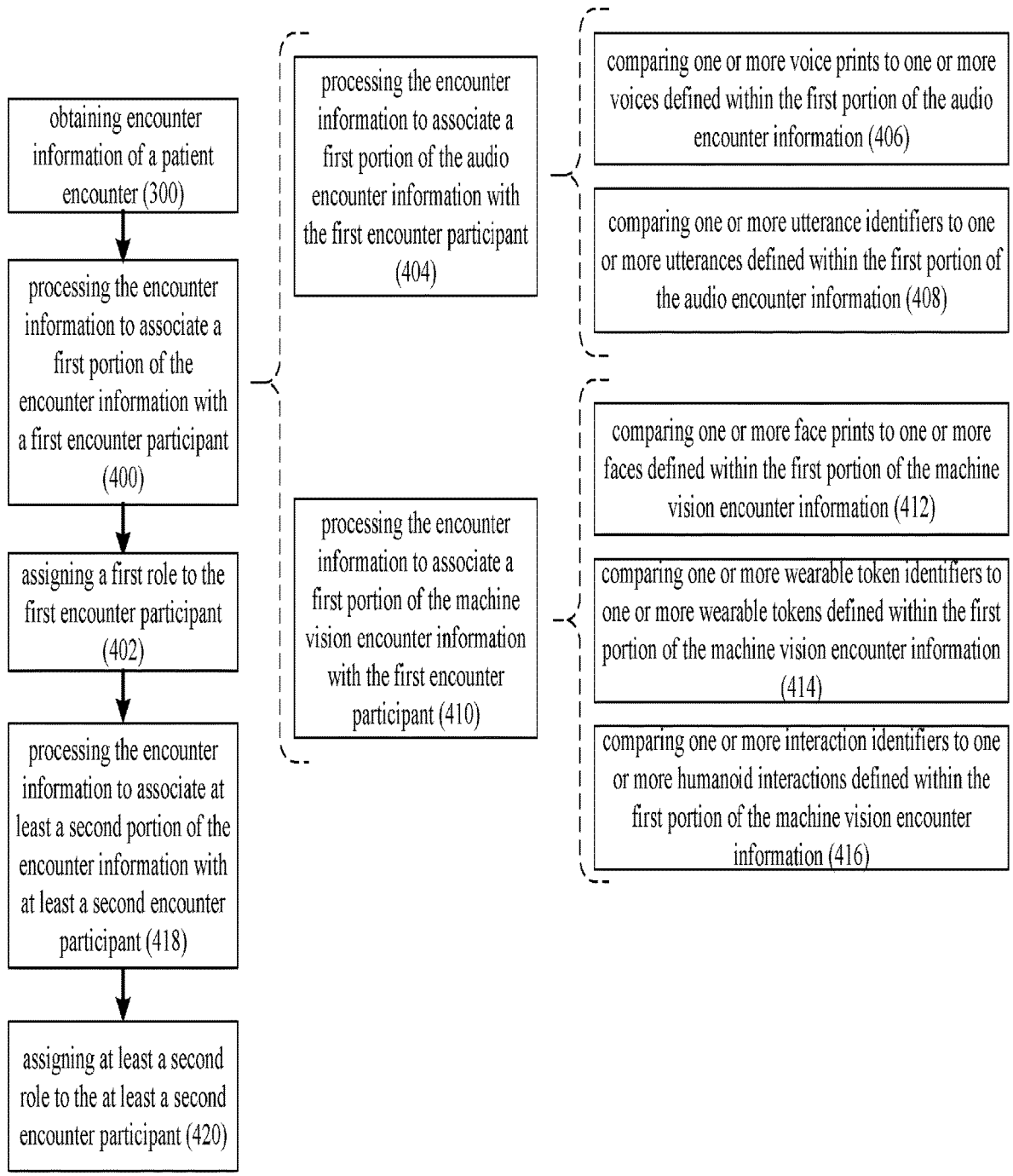
FIG. 6 is a flow chart of another implementation of the ambient clinical intelligence process of FIG. 1.

Accordingly and referring also to FIG. 6, ambient clinical intelligence process 10 may be configured to obtain 300 encounter information (e.g., machine vision encounter information 102 and/or audio encounter information 106) of a patient encounter (e.g., a visit to a doctor's office).

Ambient clinical intelligence process 10 may then process 400 the encounter information (e.g., machine vision encounter information 102 and/or audio encounter information 106) to associate a first portion of the encounter information with a first encounter participant (e.g., encounter participant 226) and assign 402 a first role to the first encounter participant (e.g., encounter participant 226).

When processing 400 the encounter information (e.g., machine vision encounter information 102 and/or audio encounter information 106) to associate the first portion of the encounter information with the first encounter participant (e.g., encounter participant 226), ambient clinical intelligence process 10 may process 404 the encounter information (e.g., machine vision encounter information 102 and/or audio encounter information 106) to associate a first portion of the audio encounter information (e.g., audio encounter information 106A) with the first encounter participant (e.g., encounter participant 226).

Specifically and when processing 404 the encounter information (e.g., machine vision encounter information 102 and/or audio encounter information 106) to associate the first portion of the audio encounter information (e.g., audio encounter information 106A) with the first encounter participant (e.g., encounter participant 226), ambient clinical intelligence process 10 may compare 406 one or more voice prints (defined within voice print datasource) to one or more voices defined within the first portion of the audio encounter information (e.g., audio encounter information 106A); and may compare 408 one or more utterance identifiers (defined within utterance datasource) to one or more utterances defined within the first portion of the audio encounter information (e.g., audio encounter information 106A); wherein comparisons 406, 408 may allow ambient clinical intelligence process 10 to assign 402 a first role to the first encounter participant (e.g., encounter participant 226). For example, if the identity of encounter participant 226 can be defined via voice prints, a role for encounter participant 226 may be assigned 402 if that identity defined is associated with a role (e.g., the identity defined for encounter participant 226 is Doctor Susan Jones). Further, if an utterance made by encounter participant 226 is "I am Doctor Susan Jones", this utterance may allow a role for encounter participant 226 to be assigned 402.

When processing 400 the encounter information (e.g., machine vision encounter information 102 and/or audio encounter information 106) to associate the first portion of the encounter information with the first encounter participant (e.g., encounter participant 226), ambient clinical intelligence process 10 may process 410 the encounter information (e.g., machine vision encounter information 102 and/or audio encounter information 106) to associate a first portion of the machine vision encounter information (e.g., machine vision encounter information 102A) with the first encounter participant (e.g., encounter participant 226).

Specifically and when processing 410 the encounter information (e.g., machine vision encounter information 102 and/or audio encounter information 106) to associate the first portion of the machine vision encounter information (e.g., machine vision encounter information 102A) with the first encounter participant (e.g., encounter participant 226), ambient clinical intelligence process 10 may compare 412 one or more face prints (defined within face print datasource) to one or more faces defined within the first portion of the machine vision encounter information (e.g., machine vision encounter information 102A); compare 414 one or more wearable token identifiers (defined within wearable token identifier datasource) to one or more wearable tokens defined within the first portion of the machine vision encounter information (e.g., machine vision encounter information 102A); and compare 416 one or more interaction identifiers (defined within interaction identifier datasource) to one or more humanoid interactions defined within the first portion of the machine vision encounter information (e.g., machine vision encounter information 102A); wherein comparisons 412, 414, 416 may allow ambient clinical intelligence process 10 to assign 402 a first role to the first encounter participant (e.g., encounter participant 226). For example, if the identity of encounter participant 226 can be defined via face prints, a role for encounter participant 226 may be assigned 402 if that identity defined is associated with a role (e.g., the identity defined for encounter participant 226 is Doctor Susan Jones). Further, if a wearable token worn by encounter participant 226 can be identified as a wearable token assigned to Doctor Susan Jones, a role for encounter participant 226 may be assigned 402. Additionally, if an interaction made by encounter participant 226 corresponds to the type of interaction that is made by a doctor, the existence of this interaction may allow a role for encounter participant 226 to be assigned 402.

Examples of such wearable tokens may include but are not limited to wearable devices that may be worn by the medical professionals when they are within monitored space 130 (or after they leave monitored space 130). For example, these wearable tokens may be worn by medical professionals when e.g., they are moving between monitored rooms within monitored space 130, traveling to and/or from monitored space 130, and/or outside of monitored space 130 (e.g., at home).

Additionally, ambient clinical intelligence process 10 may process 418 the encounter information (e.g., machine vision encounter information 102 and/or audio encounter information 106) to associate at least a second portion of the encounter information with at least a second encounter participant; and may assign 420 at least a second role to the at least a second encounter participant.

Specifically, ambient clinical intelligence process 10 may process 418 the encounter information (e.g., machine vision encounter information 102 and/or audio encounter information 106) to associate at least a second portion of the encounter information with at least a second encounter participant. For example, ambient clinical intelligence process 10 may process 418 the encounter information (e.g., machine vision encounter information 102 and/or audio encounter information 106) to associate audio encounter information 106B and machine vision encounter information 102B with encounter participant 228 and may associate audio encounter information 106C and machine vision encounter information 102C with encounter participant 230.

Further, ambient clinical intelligence process 10 may assign 420 at least a second role to the at least a second encounter participant. For example, ambient clinical intelligence process 10 may assign 420 a role to encounter participants 228, 230.

Automated Movement Tracking

Ambient clinical intelligence process 10 may be configured to track the movement and/or interaction of humanoid shapes within the monitored space (e.g., monitored space 130) during the patient encounter (e.g., a visit to a doctor's office) so that e.g., the ambient clinical intelligence process 10 knows when encounter participants (e.g., one or more of encounter participants 226, 228, 230) enter, exit or cross paths within monitored space 130.

Figure 7:
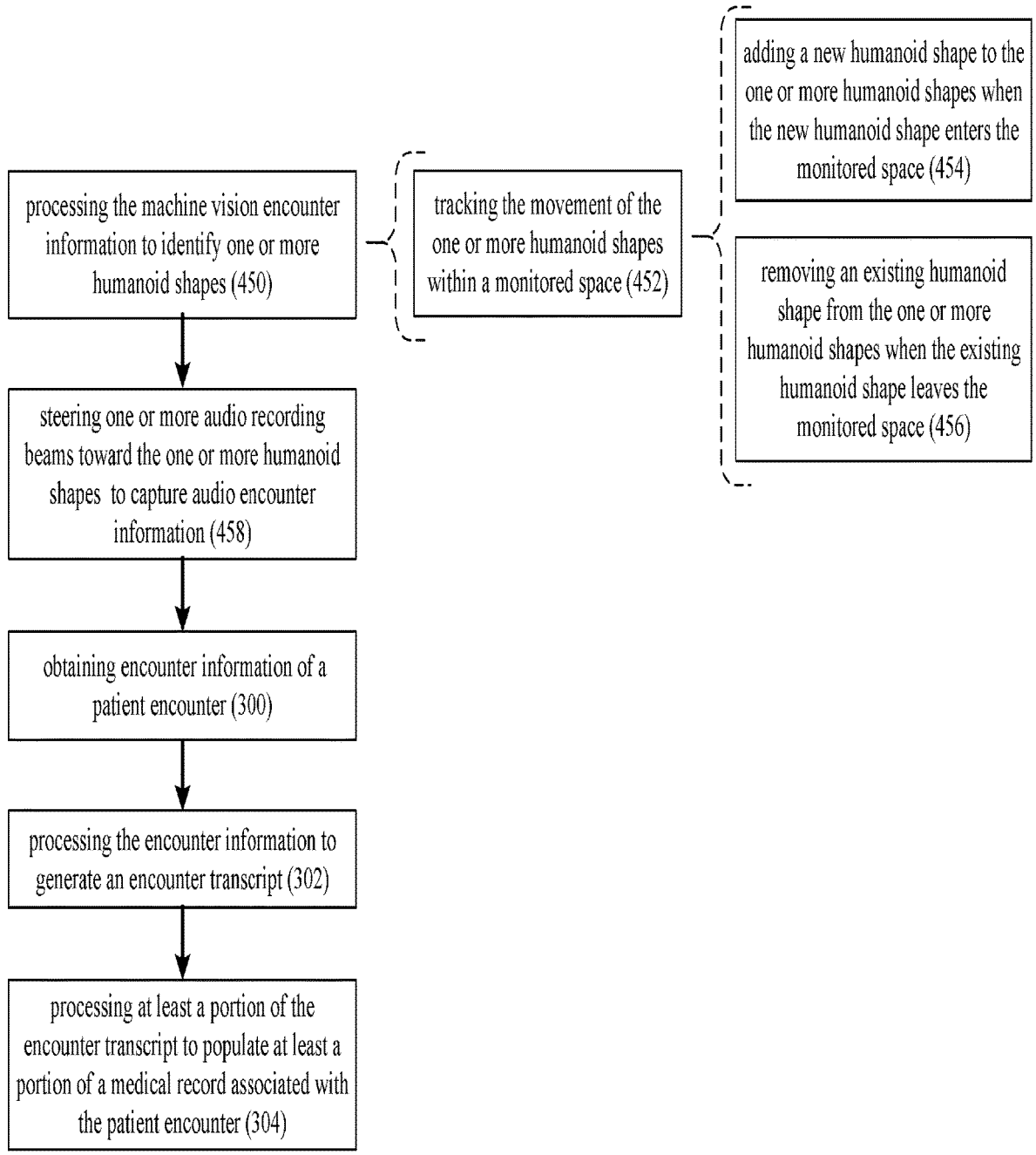
FIG. 7 is a flow chart of another implementation of the ambient clinical intelligence process of FIG. 1.

Accordingly and referring also to FIG. 7, ambient clinical intelligence process 10 may process 450 the machine vision encounter information (e.g., machine vision encounter information 102) to identify one or more humanoid shapes. As discussed above, examples of machine vision system 100 generally (and ACI client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system).

When ACI client electronic device 34 includes a visible light imaging system (e.g., an RGB imaging system), ACI client electronic device 34 may be configured to monitor various objects within monitored space 130 by recording motion video in the visible light spectrum of these various objects. When ACI client electronic device 34 includes an invisible light imaging systems (e.g., a laser imaging system, an infrared imaging system and/or an ultraviolet imaging system), ACI client electronic device 34 may be configured to monitor various objects within monitored space 130 by recording motion video in the invisible light spectrum of these various objects. When ACI client electronic device 34 includes an X-ray imaging system, ACI client electronic device 34 may be configured to monitor various objects within monitored space 130 by recording energy in the X-ray spectrum of these various objects. When ACI client electronic device 34 includes a SONAR imaging system, ACI client electronic device 34 may be configured to monitor various objects within monitored space 130 by transmitting soundwaves that may be reflected off of these various objects. When ACI client electronic device 34 includes a RADAR imaging system, ACI client electronic device 34 may be configured to monitor various objects within monitored space 130 by transmitting radio waves that may be reflected off of these various objects. When ACI client electronic device 34 includes a thermal imaging system, ACI client electronic device 34 may be configured to monitor various objects within monitored space 130 by tracking the thermal energy of these various objects.

As discussed above, ACI compute system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource.

Accordingly and when processing 450 the machine vision encounter information (e.g., machine vision encounter information 102) to identify one or more humanoid shapes, ambient clinical intelligence process 10 may be configured to compare the humanoid shapes defined within one or more datasources 118 to potential humanoid shapes within the machine vision encounter information (e.g., machine vision encounter information 102).

When processing 450 the machine vision encounter information (e.g., machine vision encounter information 102) to identify one or more humanoid shapes, ambient clinical intelligence process 10 may track 452 the movement of the one or more humanoid shapes within the monitored space (e.g., monitored space 130). For example and when tracking 452 the movement of the one or more humanoid shapes within monitored space 130, ambient clinical intelligence process 10 may add 454 a new humanoid shape to the one or more humanoid shapes when the new humanoid shape enters the monitored space (e.g., monitored space 130) and/or may remove 456 an existing humanoid shape from the one or more humanoid shapes when the existing humanoid shape leaves the monitored space (e.g., monitored space 130).

For example, assume that a lab technician (e.g., encounter participant 242) temporarily enters monitored space 130 to chat with encounter participant 230. Accordingly, ambient clinical intelligence process 10 may add 454 encounter participant 242 to the one or more humanoid shapes being tracked 452 when the new humanoid shape (i.e., encounter participant 242) enters monitored space 130. Further, assume that the lab technician (e.g., encounter participant 242) leaves monitored space 130 after chatting with encounter participant 230. Therefore, ambient clinical intelligence process 10 may remove 456 encounter participant 242 from the one or more humanoid shapes being tracked 452 when the humanoid shape (i.e., encounter participant 242) leaves monitored space 130.

Also and when tracking 452 the movement of the one or more humanoid shapes within monitored space 130, ambient clinical intelligence process 10 may monitor the trajectories of the various humanoid shapes within monitored space 130. Accordingly, assume that when leaving monitored space 130, encounter participant 242 walks in front of (or behind) encounter participant 226. As ambient clinical intelligence process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by ambient clinical intelligence process 10.

Ambient clinical intelligence process 10 may be configured to obtain 300 the encounter information of the patient encounter (e.g., a visit to a doctor's office), which may include machine vision encounter information 102 (in the manner described above) and/or audio encounter information 106.

Ambient clinical intelligence process 10 may steer 458 one or more audio recording beams (e.g., audio recording beams 220, 222, 224) toward the one or more humanoid shapes (e.g., encounter participants 226, 228, 230) to capture audio encounter information (e.g., audio encounter information 106), wherein audio encounter information 106 may be included within the encounter information (e.g., machine vision encounter information 102 and/or audio encounter information 106).

Specifically and as discussed above, ambient clinical intelligence process 10 (via modular ACI system 54 and/or audio recording system 104) may utilize one or more of the discrete audio acquisition devices (e.g., audio acquisition devices 202, 204, 206, 208, 210, 212, 214, 216, 218) to form an audio recording beam. For example, modular ACI system 54 and/or audio recording system 104 may be configured to utilize various audio acquisition devices to form audio recording beam 220, thus enabling the capturing of audio (e.g., speech) produced by encounter participant 226 (as audio recording beam 220 is pointed to (i.e., directed toward) encounter participant 226). Additionally, modular ACI system 54 and/or audio recording system 104 may be configured to utilize various audio acquisition devices to form audio recording beam 222, thus enabling the capturing of audio (e.g., speech) produced by encounter participant 228 (as audio recording beam 222 is pointed to (i.e., directed toward) encounter participant 228). Additionally, modular ACI system 54 and/or audio recording system 104 may be configured to utilize various audio acquisition devices to form audio recording beam 224, thus enabling the capturing of audio (e.g., speech) produced by encounter participant 230 (as audio recording beam 224 is pointed to (i.e., directed toward) encounter participant 230).

Once obtained, ambient clinical intelligence process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Physical Event Detection:

As discussed above and as shown in FIG. 2, modular ACI system 54 may be configured to automate clinical documentation, wherein modular ACI system 54 may include: machine vision system 100 configured to obtain machine vision encounter information 102 concerning a patient encounter; audio recording system 104 configured to obtain audio encounter information 106 concerning the patient encounter; and a compute system (e.g., ACI compute system 12) configured to receive machine vision encounter information 102 and audio encounter information 106 from machine vision system 100 and audio recording system 104 (respectively).

Machine vision system 100 may include but are not limited to: one or more ACI client electronic devices (e.g., ACI client electronic device 34, examples of which may include but are not limited to an RGB imaging system, an infrared imaging system, a ultraviolet imaging system, a laser imaging system, a SONAR imaging system, a RADAR imaging system, and a thermal imaging system).

Audio recording system 104 may include but are not limited to: one or more ACI client electronic devices (e.g., ACI client electronic device 30, examples of which may include but are not limited to a handheld microphone (e.g., one example of a body worn microphone), a lapel microphone (e.g., another example of a body worn microphone), an embedded microphone, such as those embedded within eyeglasses, smart phones, tablet computers and/or watches (e.g., another example of a body worn microphone), and an audio recording device).

Figure 8:
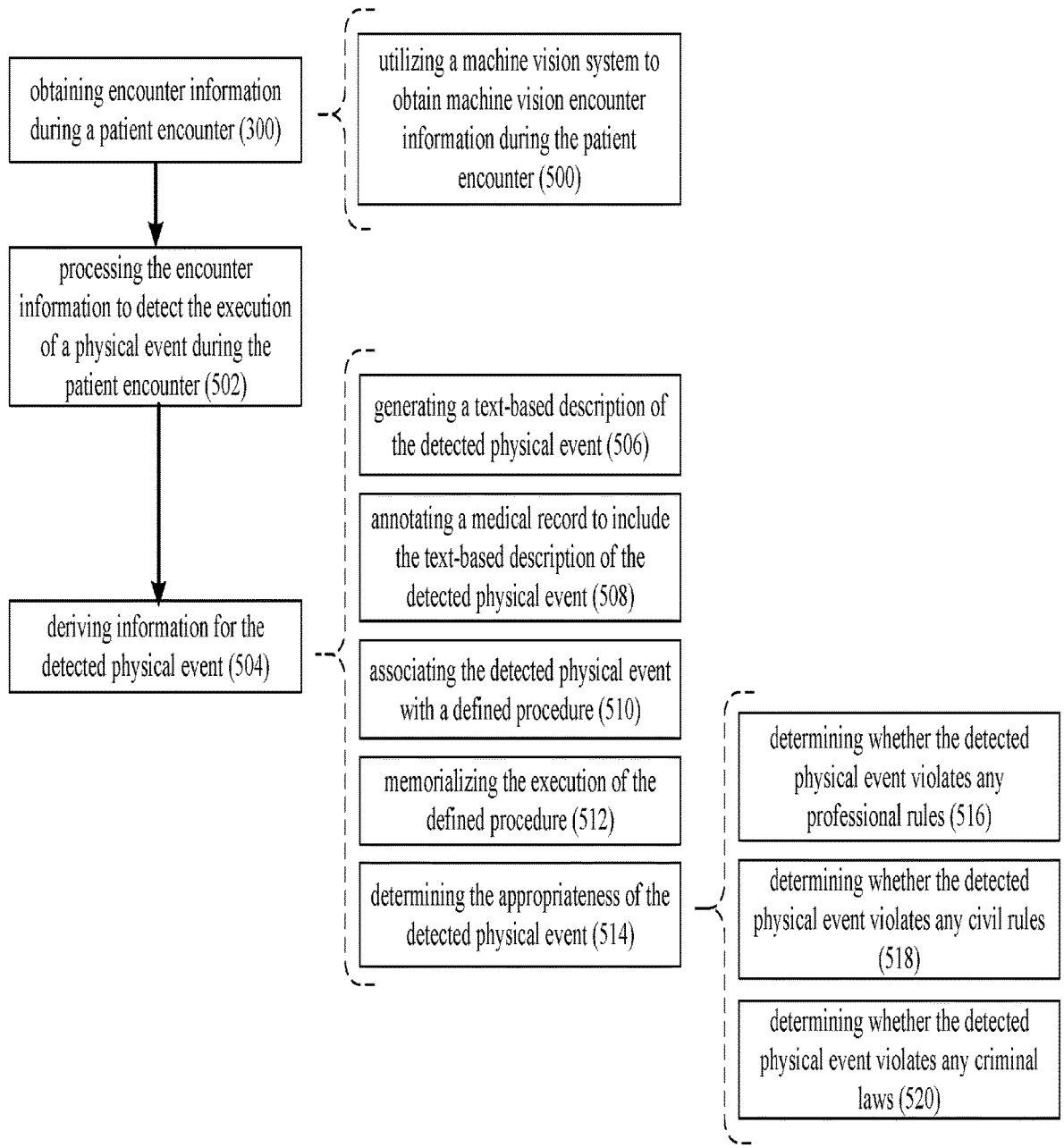
FIG. 8 is a flow chart of another implementation of the ambient clinical intelligence process of FIG. 1

As discussed above and referring also to FIG. 8, ambient clinical intelligence process 10 may be configured to obtain 300 encounter information (e.g., machine vision encounter information 102 and/or audio encounter information 106) during a patient encounter (e.g., a visit to a doctor's office). When obtaining 300 encounter information during the patient encounter (e.g., a visit to a doctor's office), ambient clinical intelligence process 10 may utilize 500 a machine vision system (e.g., machine vision system 100) to obtain 300 machine vision encounter information (e.g., machine vision encounter information 102) during the patient encounter (e.g., a visit to a doctor's office).

Once obtained 300, ambient clinical intelligence process 10 may process 502 the encounter information (e.g., machine vision encounter information 102 and/or audio encounter information 106) to detect the execution of a physical event during the patient encounter (e.g., a visit to a doctor's office), thus defining a detected physical event (e.g., detected physical event 132).

The detected physical event (e.g., detected physical event 132) may be any event that occurs during the patient encounter that is not adequately discernable via only audio encounter information 106.

Some detected physical events (e.g., detected physical event 132) may not include a verbal component, examples of which may include but are not limited to:
- a patient (e.g., encounter participant 228) limping into the monitored space (e.g., monitored space 130);
- a patient (e.g., encounter participant 228) rubbing their head;
- a patient (e.g., encounter participant 228) pointing to a portion of their body to indicate the location of their pain to a medical professional (e.g., encounter participant 226);
- a patient (e.g., encounter participant 228) performing a range-of-motion test for a medical professional (e.g., encounter participant 226);
- a medical professional (e.g., encounter participant 226) examining the lymph nodes of a patient (e.g., encounter participant 228); and
- a medical professional (e.g., encounter participant 226) palpitating the abdomen of a patient (e.g., encounter participant 228).

However, some detected physical events (e.g., detected physical event 132) may be associable with a verbal component, examples of which may include but are not limited to:
- a patient (e.g., encounter participant 228) pointing to a portion of their body to indicate the location of their pain in response to a physician (e.g., encounter participant 226) asking them "Where does it hurt?";
- a patient (e.g., encounter participant 228) performing a range-of-motion test for a physician (e.g., encounter participant 226) in response to the physician (e.g., encounter participant 226) instructing them to "Hold your arms out straight from your side and touch them above your head"; and
- a patient (e.g., encounter participant 228) attempting to touch their toes in response to a physician (e.g., encounter participant 226) asking them to "Please try to touch your toes without bending your knees".

Further still, some detected physical events (e.g., detected physical event 132) may include the use of a physical device (e.g., when a medical professional uses a medical device), examples of which may include but are not limited to:
- a medical professional (e.g., encounter participant 226) looking into the mouth of patient (e.g., encounter participant 228) using a handheld light;
- a medical professional (e.g., encounter participant 226) listening to the respiratory function of a patient (e.g., encounter participant 228) using a stethoscope;
- a medical professional (e.g., encounter participant 226) listening to the heart of a patient (e.g., encounter participant 228) using a stethoscope; and
- a medical professional (e.g., encounter participant 226) taking the blood pressure of a patient (e.g., encounter participant 228) using a blood pressure cuff, meter and stethoscope.

Once a physical event (e.g., detected physical event 132) is detected, ambient clinical intelligence process 10 may derive 504 information for the detected physical event (e.g., detected physical event 132). The information derived for the detected physical event may include: machine vision encounter information; and audio encounter information. As discussed above, some detected physical events (e.g., detected physical event 132) may be associable with a verbal component. Accordingly and in such a situation, the information derived for the detected physical event may include both machine vision encounter information and audio encounter information. As discussed above, ACI compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, a physical events datasource, and a home healthcare datasource.

Accordingly, such a physical events datasource may be configured to define one or more of the above-described physical events, wherein ambient clinical intelligence process 10 may be configured to access such a physical events datasource when processing 502 the encounter information (e.g., machine vision encounter information 102 and/or audio encounter information 106) to detect the execution of a physical event during the patient encounter (e.g., a visit to a doctor's office) and derive 504 information for the detected physical event (e.g., detected physical event 132). For example, ambient clinical intelligence process 10 may compare the encounter information (e.g., machine vision encounter information 102 and/or audio encounter information 106) to the physical events defined within such a physical events datasource to detect the execution of a physical event during the patient encounter (e.g., a visit to a doctor's office) and derive 504 information for the detected physical event (e.g., detected physical event 132).

When deriving 504 information for the detected physical event (e.g., detected physical event 132), ambient clinical intelligence process 10: may generate 506 a text-based description of the detected physical event (e.g., detected physical event 132); and may annotate 508 a medical record to include the text-based description of the detected physical event (e.g., detected physical event 132).

For example, in a situation where a patient (e.g., encounter participant 228) pointed to their left knee to indicate the location of their pain to a medical professional (e.g., encounter participant 226), ambient clinical intelligence process 10: may generate 506 a text-based description (e.g., "Patient pointed to left knee with right hand") of the detected physical event (e.g., detected physical event 132); and may annotate 508 a medical record (e.g., medical record 236) to include the text-based description (e.g., "Patient pointed to left knee with right hand") of the detected physical event (e.g., detected physical event 132).

Through the use of ambient clinical intelligence process 10, ambiguous words (e.g., this, that, here, there, those) may be disambiguated, thus allowing "Does it hurt here?" to have an understandable meaning, For example, detected physical event 132 may be a physician (e.g., encounter participant 226) pointing to the left knee of the patient (e.g., encounter participant 228) while asking "Does it hurt here?". Naturally, there must be temporal alignment for ambient clinical intelligence process 10 to utilize a detected physical event (e.g., the physician pointing to the left knee of the patient) to disambiguate "Does it hurt here?" For example, if there is a 20 minute gap between these two events, one does not add any clarity to the other; while (conversely) if these two events occur contemporaneously, one does add clarity to the other.

Further, in the situation where a patient (e.g., encounter participant 228) performed a range-of-motion test for a physician (e.g., encounter participant 226) in response to the request of a physician (e.g., encounter participant 226), ambient clinical intelligence process 10: may generate 506 a text-based description (e.g., "Patient performed range-of-motion test. Patient displayed an 88 degree range of motion in their right shoulder and a 73 degree range of motion in their left shoulder."); and may annotate 508 a medical record (e.g., medical record 236) to include the text-based description (e.g., "Patient performed range-of-motion test. Patient displayed a 88 degree range of motion in their right shoulder and a 73 degree range of motion in their left shoulder.") of the detected physical event (e.g., detected physical event 132).

For information that has values associated with it (such as the above-described range-of-motion test), this value-based information (e.g., 88 degree range of motion in right shoulder and 73 degree range of motion in left shoulder) may be compared to previous values of the same information so that the status of the patient (e.g., encounter participant 228) may be monitored over a period of time.

When deriving 504 information for the detected physical event (e.g., detected physical event 132), ambient clinical intelligence process 10 may: associate 510 the detected physical event (e.g., detected physical event 132) with a defined procedure; and memorialize 512 the execution of the defined procedure.

For example, if a patient (e.g., encounter participant 228) makes an appointment to see a medical professional (e.g., encounter participant 226) because they are not feeling well, the medical professional (e.g., encounter participant 226) may perform a "review of symptoms" procedure that may require the medical professional (e.g., encounter participant 226) to perform several defined procedures. For example: the medical professional (e.g., encounter participant 226) may (among other things):

examine the lymph nodes of the patient (e.g., encounter participant 228);
palpitate the abdomen of the patient (e.g., encounter participant 228);
look into the mouth of the patient (e.g., encounter participant 228);
listen to the respiratory function of the patient (e.g., encounter participant 228);
listen to the heart of the patient (e.g., encounter participant 228); and
take a blood pressure reading of the patient (e.g., encounter participant 228).

Oftentimes, medical best practices (or medical insurance providers) require that a defined number of procedures be performed whenever a patient (e.g., encounter participant 228) visits a medical professional (e.g., encounter participant 226), wherein the performance of these procedures may be required to e.g., be paid by the medical insurance provider, avoid malpractice claims, adhere to the requirements of their employer, etc.

Accordingly and when deriving 504 information for the detected physical event (e.g., detected physical event 132), ambient clinical intelligence process 10 may associate 510 the detected physical event (e.g., detected physical event 132) with a defined procedure (e.g., examining the lymph nodes, palpitating the abdomen, looking into the mouth, listening to the respiratory function, listening to the heart, or taking a blood pressure reading). Ambient clinical intelligence process 10 may then memorialize 512 the execution of the defined procedure by e.g., annotating 508 a medical record (e.g., medical record 236).

Further and when deriving 504 information for the detected physical event (e.g., detected physical event 132), ambient clinical intelligence process 10 may: determine 514 the appropriateness of the detected physical event (e.g., detected physical event 132) to e.g., determine the appropriateness of the interaction between the patient (e.g., encounter participant 228) and the medical professional (e.g., encounter participant 226).

For example and when determining 514 the appropriateness of the detected physical event (e.g., detected physical event 132), ambient clinical intelligence process 10:
may determine 516 whether the detected physical event (e.g., detected physical event 132) violates any professional rules;
may determine 518 whether the detected physical event (e.g., detected physical event 132) violates any civil rules; and/or
may determine 520 whether the detected physical event (e.g., detected physical event 132) violates any criminal laws.

For example, did the detected physical event (e.g., detected physical event 132) indicate that the medical professional (e.g., encounter participant 226) inappropriately touched the patient (e.g., encounter participant 228). If so, did that inappropriate touching violate any professional rules, civil rules or criminal rules?

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
   obtaining encounter information during a patient encounter, wherein the encounter information includes machine vision encounter information and audio encounter information;
   processing the machine vision encounter information and the audio encounter information of the encounter information to detect the execution of a physical event during the patient encounter, thus defining a detected physical event, wherein the detected physical event is associable with a verbal component identified in the audio encounter information and the physical event identified in the machine vision encounter information, wherein the detected physical event is identified, at least in part, by comparing the machine vision encounter information to a physical events datasource; and deriving information for the detected physical event by generating a text-based description of the detected physical event and annotating a medical record to include the text-based description of the detected physical event, wherein the information derived for the detected physical event includes the machine vision encounter information and the audio encounter information, wherein deriving the information for the detected physical event includes:

monitoring a status of a patient over a period of time by comparing numeric values of the information derived for the detected physical event in the annotated medical record to previous numeric values of the information derived for the detected physical event in the annotated medical record, and determining the appropriateness of the detected physical event based upon, at least in part, the text-based description of the detected physical event.

2. The computer-implemented method of claim 1 wherein obtaining encounter information during a patient encounter includes:

utilizing a machine vision system to obtain machine vision encounter information during the patient encounter.

3. The computer-implemented method of claim 1 wherein deriving information for the detected physical event includes:

associating the detected physical event with a defined procedure; and memorializing the execution of the defined procedure.

4. The computer-implemented method of claim 1 wherein determining the appropriateness of the detected physical event includes one or more of:

determining whether the detected physical event violates any professional rules;

determining whether the detected physical event violates any civil rules; and determining whether the detected physical event violates any criminal laws.

5. The computer-implemented method of claim 1 wherein the detected physical event includes the use of a physical device.

6. A computer program product residing on a non-transitory computer readable medium having a plurality of instructions stored thereon which, when executed by a processor, cause the processor to perform operations comprising:

obtaining encounter information during a patient encounter, wherein the encounter information includes machine vision encounter information and audio encounter information;

processing the machine vision encounter information and the audio encounter information of the encounter information to detect the execution of a physical event during the patient encounter, thus defining a detected physical event, wherein the detected physical event is associable with a verbal component identified in the audio encounter information and the physical event identified in the machine vision encounter information, wherein the detected physical event is identified, at least in part, by comparing the machine vision encounter information to a physical events datasource; and deriving information for the detected physical event by generating a text-based description of the detected physical event and annotating a medical record to include the text-based description of the detected physical event, wherein the information derived for the detected physical event includes the machine vision encounter information and the audio encounter information, wherein deriving the information for the detected physical event includes:

monitoring a status of a patient over a period of time by comparing numeric values of the information derived for the detected physical event in the annotated medical record to previous numeric values of the information derived for the detected physical event in the annotated medical record, and determining the appropriateness of the detected physical event based upon, at least in part, the text-based description of the detected physical event.

7. The computer program product of claim 6 wherein obtaining encounter information during a patient encounter includes:

utilizing a machine vision system to obtain machine vision encounter information during the patient encounter.

8. The computer program product of claim 6 wherein deriving information for the detected physical event includes:

associating the detected physical event with a defined procedure; and memorializing the execution of the defined procedure.

9. The computer program product of claim 6 wherein determining the appropriateness of the detected physical event includes one or more of:

determining whether the detected physical event violates any professional rules;

determining whether the detected physical event violates any civil rules; and determining whether the detected physical event violates any criminal laws.

10. The computer program product of claim 6 wherein the detected physical event includes the use of a physical device.

11. A computing system including a processor and memory configured to perform operations comprising:

obtaining encounter information during a patient encounter, wherein the encounter information includes machine vision encounter information and audio encounter information;

processing the machine vision encounter information and the audio encounter information of the encounter information to detect the execution of a physical event during the patient encounter, thus defining a detected physical event, wherein the detected physical event is associable with a verbal component identified in the audio encounter information and the physical event identified in the machine vision encounter information, wherein the detected physical event is identified, at least in part, by comparing the machine vision encounter information to a physical events datasource; and deriving information for the detected physical event by generating a text-based description of the detected physical event and annotating a medical record to include the text-based description of the detected physical event, wherein the information derived for the detected physical event includes the machine vision encounter information and the audio encounter information, wherein deriving the information for the detected physical event includes:

monitoring a status of a patient over a period of time by comparing numeric values of the information derived for the detected physical event in the annotated medical record to previous numeric values of the information derived for the detected physical event in the annotated medical record, and determining the appropriateness of the detected physical event based upon, at least in part, the text-based description of the detected physical event.

12. The computing system of claim 11 wherein obtaining encounter information during a patient encounter includes:

utilizing a machine vision system to obtain machine vision encounter information during the patient encounter.

13. The computing system of claim 11 wherein deriving information for the detected physical event includes:

associating the detected physical event with a defined procedure; and memorializing the execution of the defined procedure.

14. The computing system of claim 11 wherein determining the appropriateness of the detected physical event includes one or more of:

determining whether the detected physical event violates any professional rules;

determining whether the detected physical event violates any civil rules; and determining whether the detected physical event violates any criminal laws.

15. The computing system of claim 11 wherein the detected physical event includes the use of a physical device.

* * * * *